United States Patent [19]

Lee

[11] Patent Number: 5,734,058
[45] Date of Patent: Mar. 31, 1998

[54] FLUORESCENT DNA-INTERCALATING CYANINE DYES INCLUDING A POSITIVELY CHARGED BENZOTHIAZOLE SUBSTITUENT

[75] Inventor: Linda G. Lee, Palo Alto, Calif.

[73] Assignee: Biometric Imaging, Inc., Mountain View, Calif.

[21] Appl. No.: 555,529

[22] Filed: Nov. 9, 1995

[51] Int. Cl.$^6$ .............. C07D 401/08; C07D 413/08; C07D 417/08

[52] U.S. Cl. .............. 546/176; 546/268.7; 546/269.1; 436/800

[58] Field of Search .............. 546/176, 268.7, 546/269.1; 436/800

[56] References Cited

U.S. PATENT DOCUMENTS

| | | | |
|---|---|---|---|
| 3,282,932 | 11/1966 | Lincoln et al. | 544/300 |
| 3,437,659 | 4/1969 | Larive et al. | 548/150 |
| 3,821,205 | 6/1974 | Funia, Jr. et al. | 546/176 |
| 4,323,362 | 4/1982 | Degen et al. | 8/506 |
| 4,600,776 | 7/1986 | Meisel et al. | 544/198 |
| 4,677,051 | 6/1987 | Kubodera | 430/550 |
| 4,751,309 | 6/1988 | Daltrozzo | 546/176 |
| 4,847,364 | 7/1989 | Mockli | 534/605 |
| 4,957,870 | 9/1990 | Lee et al. | 436/63 |
| 5,321,130 | 6/1994 | Yue et al. | 536/23.1 |
| 5,401,847 | 3/1995 | Glazer | 546/107 |
| 5,410,030 | 4/1995 | Yue et al. | 536/23.1 |
| 5,436,134 | 7/1995 | Haughland et al. | 435/34 |
| 5,534,416 | 7/1996 | Millard et al. | 436/34 |
| 5,545,535 | 8/1996 | Roth | 435/34 |

FOREIGN PATENT DOCUMENTS

WO 93/06482  4/1993  WIPO.

OTHER PUBLICATIONS

Becker, et al., *J. Am. Chem. Soc.* 1979, 101, 3664–3666.
Gaugain, et al., *Biochemistry* 1978, 17, 5071–5078.
Johnson, et al., Poster #1806 at 1992 *Biophysical Society/ASBMB*, Houston, TX.
Benson, et al. *Nucleid Acids Research* 1993, 21, 5720–5726.
Rye, et al. *Nucleic Acids Research* 1992, 20, 2803–2812.
Brooker, et al. *JACS* 1945, 67, 1889–1893.
Ambrogi, et al. *Synthesis* 1992, No. 7, 656–658.
Lee, et al. *Cytometry* 1986, No. 7, 508–517.
Chemical Abstracts No. 123: 1599968 Vol. 123, Frey et al., *Cytometry*, 1995, Vol. 20, No. 3, pp. 218–227.
Chemical Abstracts No. 119:67272, Vol. 119, Yue et al., WO9306482, Apr. 1, 1993.

*Primary Examiner*—C Warren Ivy
*Assistant Examiner*—D. Margaret M. Mach
*Attorney, Agent, or Firm*—Fulwider Patton Lee & Utecht, LLP

[57] ABSTRACT

New intercalating cyanine dyes are provided in which the benzothiazole portion of the cyanine dye has been modified to produce dyes with improved properties for labelling nucleic acids. The fluorescent cyanine dyes have a positively charged substituent attached to the positively charged nitrogen on the benzothiazole portion of the cyanine dye.

14 Claims, No Drawings

FLUORESCENT DNA-INTERCALATING CYANINE DYES INCLUDING A POSITIVELY CHARGED BENZOTHIAZOLE SUBSTITUENT

FIELD OF THE INVENTION

The present invention relates generally to dyes for labelling nucleic acids. More specifically, the present invention relates to intercalating cyanine dyes for the detection and enumeration of nucleic acids.

BACKGROUND OF THE INVENTION

Intercalating dyes which exhibit enhanced fluorescence upon binding to DNA or RNA are a basic tool in molecular and cell biology. In general, intercalating dyes bind noncovalently to DNA through a combination of hydrophobic interactions with the DNA base-pairs and ionic binding to the negatively charged phosphate backbone. The fluorescence of the dye is ideally increased several-fold upon binding to DNA, thereby enabling the detection of small amounts of nucleic acids. Examples of fluorescent noncovalent DNA binding dyes include ethidium bromide which is commonly used to stain DNA in agarose gels after gel electrophoresis, and propidium iodide and Hoechst 33258 which are used in flow cytometry to determine the DNA ploidy of cells.

Fluorescent nucleic acid labelling dyes preferably absorb light between about 300 and 900 nm and preferably have a Stokes shift of at least about 10 nm. Dyes that absorb light in the 500 to 900 nm range are preferred because they are spectrally removed from other components that may be present in a biological sample and because they may be used with inexpensive light sources. Fluorescent dyes that have a high extinction coefficient, a high quantum yield, and significantly enhanced fluorescence when bound to a nucleic acid are also preferred.

Few new dye chromophores were described until the introduction of Thiazole Orange as a reticulocyte stain in 1986. Lee, et al., "Thiazole Orange: A New Dye for Reticulocyte Analysis", Cytometry 1986 7, 508–517. Thiazole Orange is an asymmetric cyanine dye. Although many asymmetric cyanine dyes have been described in the art (e.g., Lincoln, et al., U.S. Pat. No. 3,282,932), Thiazole Orange's fluorescence properties when bound to DNA and RNA and its utility for labelling nucleic acids had not been previously identified. Lee, et al., U.S. Pat. No. 4,957,870. For example, unlike most asymmetric cyanine dyes, Thiazole Orange exhibits a several thousand-fold enhancement in fluorescence upon binding to DNA.

Since the discovery of Thiazole Orange as a nucleic acid dye, several improvements to Thiazole Orange and its trimethine homologs have been developed to provide dyes with tighter binding to DNA and greater water solubility. Xue, et al. U.S. Pat. No. 5,321,130 and Glazer, et al. U.S. Pat. No. 5,312,921. These dyes generally involve a modification to the quinolinium portion of the dye.

A continuing need exists for new and improved dyes for labelling nucleic acids. In particular, a need exists for dyes which exhibit longer wavelengths and significantly enhanced fluorescence when bound to DNA or RNA.

SUMMARY OF THE INVENTION

The present invention relates asymmetric cyanine dyes for noncovalently labelling nucleic acids in which the benzothiazole portion of the dye has been modified to provide improved physical properties to the dye, such as longer wavelengths and improved fluorescence enhancement when bound to DNA or RNA.

More specifically, the invention relates to fluorescent cyanine dyes having a positively charged substituent attached to the positively charged nitrogen on the benzothiazole portion of the cyanine dye. This class of fluorescent cyanine dyes are represented by the general formula

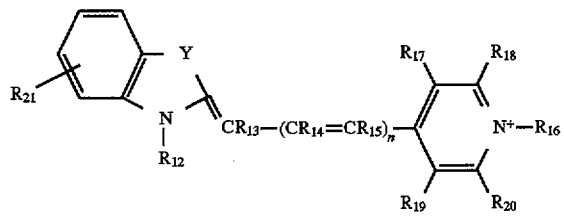

where:

n is 0, 1 or 2;

Y may be either S or O;

$R_{12}$ is a positively charged alkyl substituent, more preferably a positively charged aminoalkyl substituent;

$R_{13}$, $R_{14}$ and $R_{15}$ may each independently be either hydrogen, $C_1$–$C_{10}$ alkyl, $C_1$–$C_{10}$ alkoxy, or $C_1$–$C_{10}$ alkylthio;

$R_{12}$ and $R_{13}$ may optionally be taken together to form a 5, 6, 7 or 8 membered ring;

$R_{16}$ may be a $C_1$–$C_{50}$ alkyl, preferably substituted with one or more polar substituents which preferably includes one or more positively charged atoms, or a cyclized fluorescent cyanine dye of the present invention, i.e., where $R_{16}$ is a linker between two cyclized fluorescent cyanine dyes;

$R_{17}$ and $R_{18}$ may each independently be either H or $C_{1-10}$ alkyl, or may be taken together to form a 5 or 6 membered ring, most preferably a 6 membered aromatic ring, optionally substituted with $C_{1-6}$ alkyl or $C_1$–$C_{10}$ alkoxy groups;

$R_{19}$ and $R_{20}$ may each independently be either H or $C_{1-10}$ alkyl, or may be taken together to form a 5 or 6 membered ring, most preferably a 6 membered aromatic ring, optionally substituted with $C_1$–$C_{1-6}$ alkyl or $C_{10}$ alkoxy groups; and $R_{21}$ may be either H, $C_{1-6}$ alkyl, $C_1$–$C_{10}$ alkoxy or a fused benzene.

As used above, alkyl and alkoxy refer to any substituent having a carbon backbone having the specified range of carbon atoms. The carbon backbone may form a straight chain, may be branched or may be cyclic. The alkyl and alkoxy groups may be optionally substituted by a wide variety of substituents including, for example, alcohols, amines, thiols, phosphates, halides, ethers, esters, ketones, aldehydes, carboxylic acids, amides, cycloalkyls, and aromatic rings.

In general, $R_{12}$ can be an aminoalkyl chain containing a backbone of 3–42 carbons and 1–5 positively charged nitrogen atoms as described in U.S. Pat. No. 5,321,130 to Yue, et al. which is incorporated herein by reference. In addition to the positively charged substituents described in U.S. Pat. No. 5,321,130, $R_{12}$ is also intended to include aminoalkyl chains including a positively charged cyclic aminoalkyl group having 1–5 positively charged nitrogen atoms.

In a preferred embodiment, $R_{12}$ has the general formula —$R_{28}N(R_{29}R_{30}R_{31})$ where $R_{28}$ is a $C_{1-5}$ alkyl and $R_{29}$, $R_{30}$, and $R_{31}$ are each independently a $C_{1-10}$ alkyl.

In an alternate preferred embodiment, $R_{12}$ and $R_{13}$ are taken together to form a 5, 6, 7 or 8 membered ring where the ring includes a positively charged alkyl substituent, more preferably an aminoalkyl chain containing a backbone of 3–42 carbons and 1–5 positively charged nitrogen atoms as described in U.S. Pat. No. 5,321,130 to Yue, et al. Dyes of this embodiment may be generally represented by the general formula

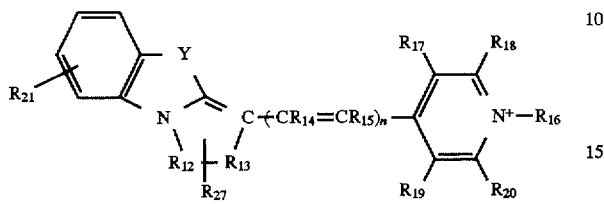

where $R_{12}$ and $R_{13}$ represent the atoms necessary to form a 5, 6, 7 or 8 membered ring and $R_{27}$ is a positively charged alkyl substituent, as specified above with regard to $R_{12}$, which may be attached to any atom used to form the 5, 6, 7 or 8 membered ring as represented by $R_{12}$ and $R_{13}$.

As used above, alkyl and alkoxy refer to any substituent having a carbon backbone having the specified range of carbon atoms, whether substituted or unsubstituted. The alkyl and alkoxy groups may be optionally substituted by a wide variety of substituents including, for example, alcohols, amines, thiols, phosphates, halides, ethers, esters, ketones, aldehydes, carboxylic acids, amides, cycloalkyls, and aromatic rings.

The invention also relates to the composition of a cyanine dye of the present invention non-covalently bound to a nucleic acid sequence, i.e., RNA or DNA, which enables the nucleic acid sequence to be analytically detected.

The invention also relates to a method for detecting nucleic acids in a sample by contacting the nucleic acids with a fluorescent cyanine dye of the present invention and monitoring the change in fluorescence emission of the dye.

DETAILED DESCRIPTION OF THE INVENTION

The present invention relates asymmetric cyanine dyes for non-covalently labelling nucleic acids in which the benzothiazole portion of the dye has been modified to provide improved physical properties to the dye, such as longer wavelengths and improved fluorescence enhancement when bound to DNA or RNA.

In one embodiment, the present invention relates to cyclized fluorescent cyanine dyes generally represented by General Formula I

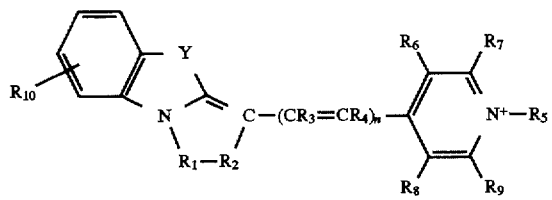

where:

n is 0, 1 or 2;

Y may be either S or O;

$R_1$ and $R_2$ are taken together to form a 5, 6, 7 or 8 membered ring;

$R_3$ and $R_4$ may each independently be either hydrogen, $C_1$–$C_{10}$ alkyl, $C_1$–$C_{10}$ alkoxy, or $C_1$–$C_{10}$ alkylthio;

$R_5$ may be a $C_1$–$C_{50}$ alkyl, preferably substituted with one or more polar substituents which preferably includes one or more positively charged atoms, or a cyclized fluorescent cyanine dye of the present invention, i.e., where $R_5$ is a linker between two cyclized fluorescent cyanine dyes;

$R_6$ and $R_7$ may each independently be either H or $C_{1\text{-}10}$ alkyl, or may be taken together to form a 5 or 6 membered ring, most preferably a 6 membered aromatic ring, optionally substituted with $C_{1\text{-}6}$ alkyl or $C_1$–$C_{10}$ alkoxy groups;

$R_8$ and $R_9$ may each independently be either H or $C_{1\text{-}10}$ alkyl, or may be taken together to form a 5 or 6 membered ring, most preferably a 6 membered aromatic ring, optionally substituted with $C_{1\text{-}6}$ alkyl or $C_1$–$C_{10}$ alkoxy groups; and $R_{10}$ may be either H, $C_{1\text{-}6}$ alkyl, $C_1$–$C_{10}$ alkoxy or a fused benzene.

As used above, alkyl and alkoxy refer to any substituent having a carbon backbone having the specified range of carbon atoms. The carbon backbone may form a straight chain, may be branched or may be cyclic. The alkyl and alkoxy groups may be optionally substituted by a wide variety of substituents including, for example, alcohols, amines, thiols, phosphates, halides, ethers, esters, ketones, aldehydes, carboxylic acids, amides, cycloalkyls, and aromatic rings.

The cyclized cyanine dyes of the present invention provide the advantage over previous cyanine dyes of having higher absorbance and emission wavelengths. The cyclized cyanine dyes preferably absorb light at a wavelength of at least about 640 nm, more preferably at least about 649 nm and emit fluorescence at a wavelength of at least about 650 nm, more preferably at least about 663 nm. The cyclized cyanine dyes also preferably have a positive Stoke's shift ($\lambda_{Emission}$-$\lambda_{Abs}$) of at least about 12 nm.

In particular, cyclized cyanine dyes having General Formula I where $R_1$ and $R_2$ are taken together to form a 5, 6, 7 or 8 membered ring have been found to absorb light and fluoresce when bound to a nucleic acid polymer at unexpectedly higher wavelengths than has been previously achieved by cyanine dyes where $R_1$ and $R_2$ do not form a ring structure.

Fluorescent cyanine dyes having the General Formula I where $R_1$ and $R_2$ are taken together to form a 7 membered ring have also been found to have the greatest Stoke's shift ($\lambda_{Emission}$-$\lambda_{Abs}$).

TABLE 1

Absorbance and Emission Maxima of Intercalating Dyes in PBS with Excess DNA ([bp]/[dye] = 100)

| COMPOUND | | $Abs_{max}$ | $Ems_{max}$ | F.E. |
|---|---|---|---|---|
| (structure) | 1 | 649 | 663 | 100X |
| (structure) | 2 | 654 | 667 | 100X |
| (structure) | 3 | 654 | 672 | 30X |
| (structure) | 4 | 675 | 690 | 200X |
| (structure) | 5* | 641 | 655 | 100X |

$Abs_{max}$ - Absorbance maximum (bound to DNA)
$Ems_{max}$ - Emission maximum (bound to DNA)
F.E. - fluorescence enhancement (bound vs. not bound to DNA or RNA)
*Compound 5 is taught in U.S. Pat. No. 5,321,130 to Yue, et al.

Table 1 summarizes the absorbance maximum and fluorescence emission maximum wavelengths (both when bound to DNA) of some exemplary cyclized cyanine dyes of the present invention.

As illustrated in Table 1, it was found that the addition of a cyclic aliphatic side chain to the basic cyanine dye structure, i.e., formation of a 5–8 membered ring by combining $R_1$ and $R_2$, was found to increase the absorbance and fluorescence emission wavelengths of the corresponding acyclic cyanine dye by about 12 nm. For example, as shown with regard to dyes 2 and 5, dye 2 has an $Abs_{max}$ at 654 nm as compared to 641 nm and an $Ems_{max}$ at 667 nm as compared to 655 nm. In addition, dye 4 is the longest wavelength trimethine intercalating dye yet reported.

With regard to n, n may equal 1. Accordingly, the present invention includes cyclized cyanine dyes having the General Formula II (i.e. where n=1)

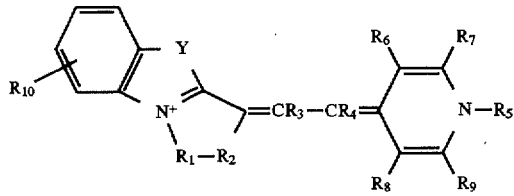

II where

Y, $R_1$, $R_2$, $R_3$, $R_4$, $R_5$, $R_6$, $R_7$, $R_8$, $R_9$ and $R_{10}$ are as specified above.

Y may be either S or O, and is most preferably S.

$R_3$ and $R_4$ may each independently be either hydrogen, $C_1$–$C_{10}$ alkyl, $C_1$–$C_{10}$ alkoxy, or $C_1$–$C_{10}$ alkylthio, and are preferably H.

$R_5$ may be a $C_1$–$C_{50}$ alkyl. Since DNA and RNA to which the cyclized cyanine dyes bind contain negatively charged phosphate backbones, it is preferred that $R_5$ be substituted with one or more polar substituents. It is most preferred that $R_5$ include one or more positively charged atoms in the polar substituent. U.S. Pat. No. 5,321,130 to Yue, et al. teaches unsymmetrical cyanine dyes having an aminoalkyl chain containing a backbone of 3–42 carbons and 1–5 positively charged nitrogen atoms. The cationic tail described in U.S. Pat. No. 5,321,130 exemplifies one of the positively charged $R_5$ substituents that may be used in combination with the cyclic cyanine dyes of the present invention and is incorporated herein by reference. In addition to the positively charged $R_5$ substituents described in U.S. Pat. No. 5,321,130, $R_{12}$ is also intended to include aminoalkyl chains including a positively charged cyclic aminoalkyl group having 1–5 positively charged nitrogen atoms.

Alternatively, $R_5$ may form part of a linker between two cyclized fluorescent cyanine dyes as illustrated by General Formula IV cyanine dyes. In general, it is preferred that the linked cyanine dyes be the same since different dyes will have different spectral properties.

$R_6$ and $R_7$ may each independently be either H, $C_{1-10}$ alkyl, or are taken together to form a 5 or 6 membered ring, most preferably a 5 or 6 membered aromatic ring, optionally substituted with $C_{1-6}$ alkyl or $C_1$–$C_{10}$ alkoxy groups.

$R_8$ and $R_9$ may each independently be either H, $C_{1-10}$ alkyl, or are taken together to form a 5 or 6 membered ring, most preferably a 5 or 6 membered aromatic ring, optionally substituted with $C_{1-6}$ alkyl or $C_1$–$C_{10}$ alkoxy groups.

In general, it is preferred either $R_6$ and $R_7$ or $R_8$ and $R_9$ are taken together to form a 5 or 6 membered aromatic ring, optionally substituted with $C_{1-6}$ alkyl or $C_1$–$C_{10}$ alkoxy groups. The $R_6$ and $R_7$ or $R_8$ and $R_9$ groups that do not form the aromatic ring are preferably H.

$R_{10}$ may be either H, $C_{1-6}$ alkyl, $C_1$–$C_{10}$ alkoxy or a fused benzene.

In a particularly preferred embodiment, the cyclized cyanine dye has the General Formula V where the ring formed by $R_1$ and $R_2$ includes a positively charged substituent $R_{27}$. As discussed herein, inclusion of a positively charged substituent, such as $R_{27}$, to a substituent on the positively charged nitrogen on the benzothiazole ring improves the net fluorescence enhancement of the dye with DNA.

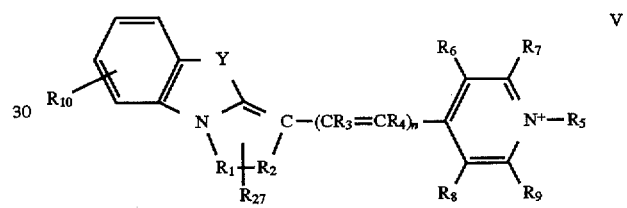

V $R_{27}$ is a positively charged alkyl substituent which may be attached to any atom used to form the 5, 6, 7 or 8 membered ring. $R_{27}$ is more preferably a positively charged aminoalkyl substituent. For example, $R_{12}$ can be an aminoalkyl chain containing a backbone of 3–42 carbons and 1–5 positively charged nitrogen atoms as described in U.S. Pat. No. 5,321,130 to Yue, et al. which is incorporated herein by reference. In addition to the positively charged substituents described in U.S. Pat. No. 5,321,130, $R_{12}$ is also intended to include aminoalkyl chains including a positively charged cyclic aminoalkyl group having 1–5 positively charged nitrogen atoms.

In a preferred embodiment, $R_{27}$ has the general formula —$R_{28}N(R_{29}R_{30}R_{31})$ where $R_{28}$ is a $C_{1-5}$ alkyl and $R_{29}$, $R_{30}$, and $R_{31}$ are each independently a $C_{1-10}$ alkyl.

Table 2 provides examples of some of the preferred cyclized cyanine dyes. It should be understood, however, that the dyes listed in Table 2 are intended only to exemplify

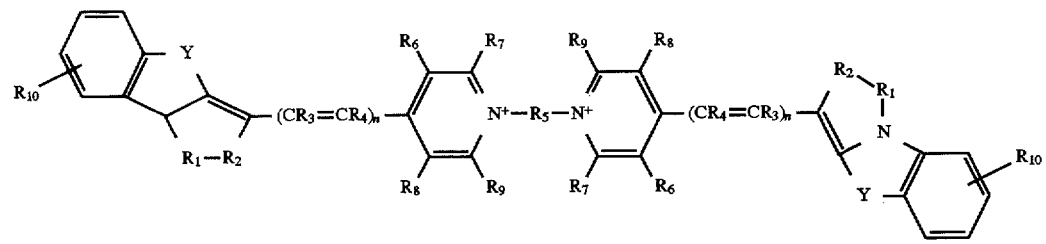

IV

According to this embodiment, Y, $R_1$, $R_2$, $R_3$, $R_4$, $R_6$, $R_7$, $R_8$, $R_9$ and $R_{10}$ are as specified above. It should be noted that the two linked cyanine dyes may be the same or different the cyclized cyanine dyes of the present invention and are not intended to be limiting.

TABLE 2
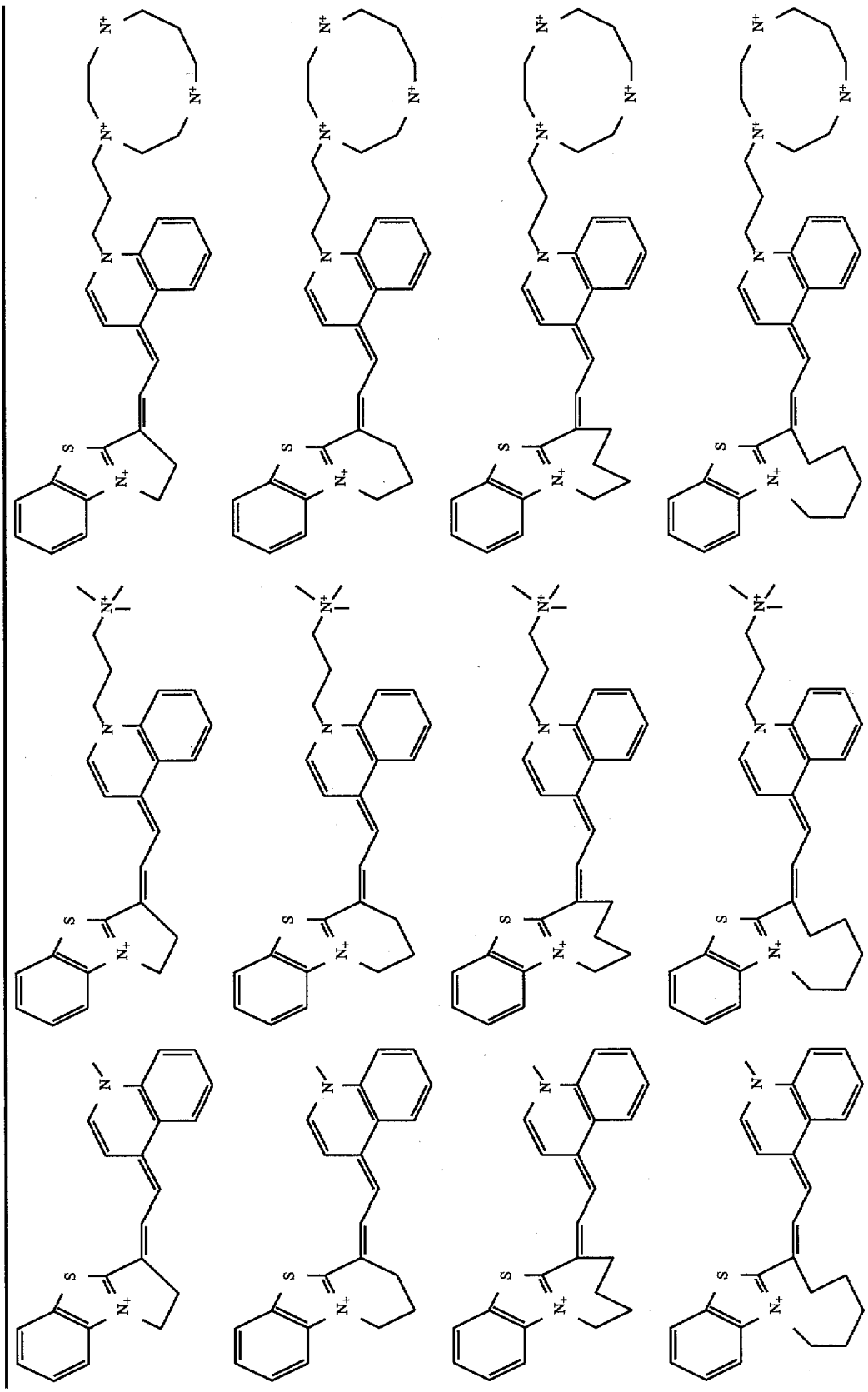

TABLE 2-continued
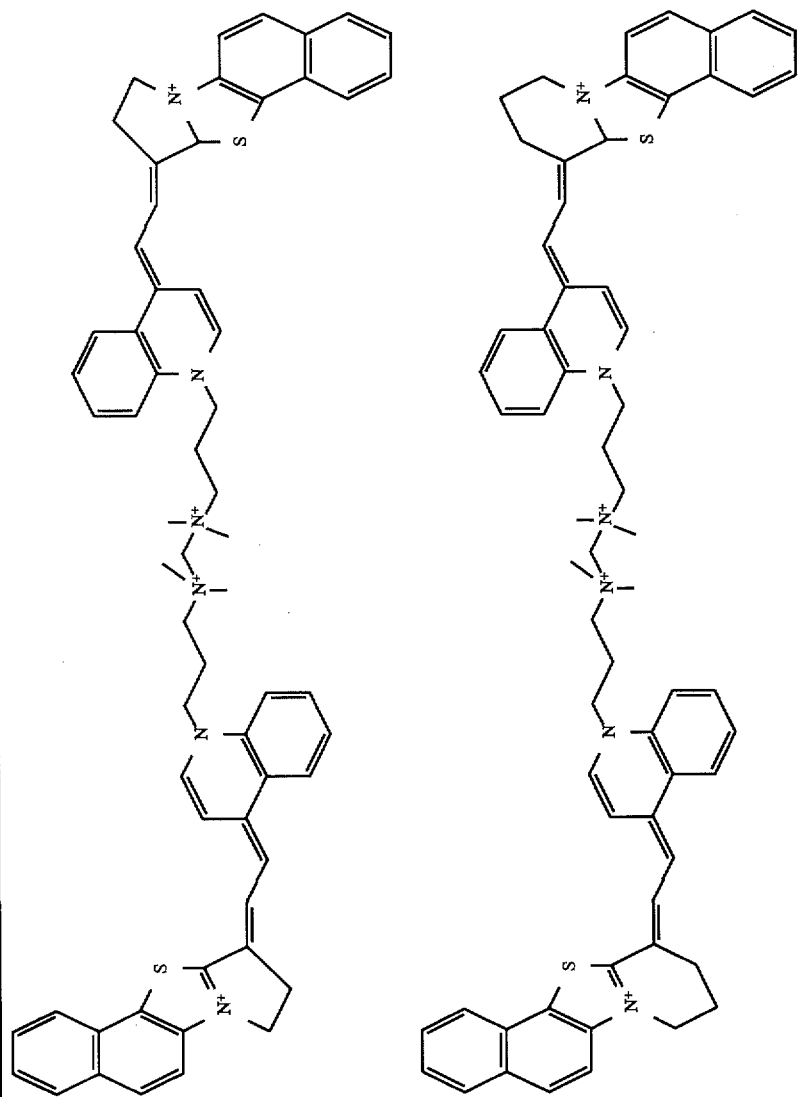

TABLE 2-continued
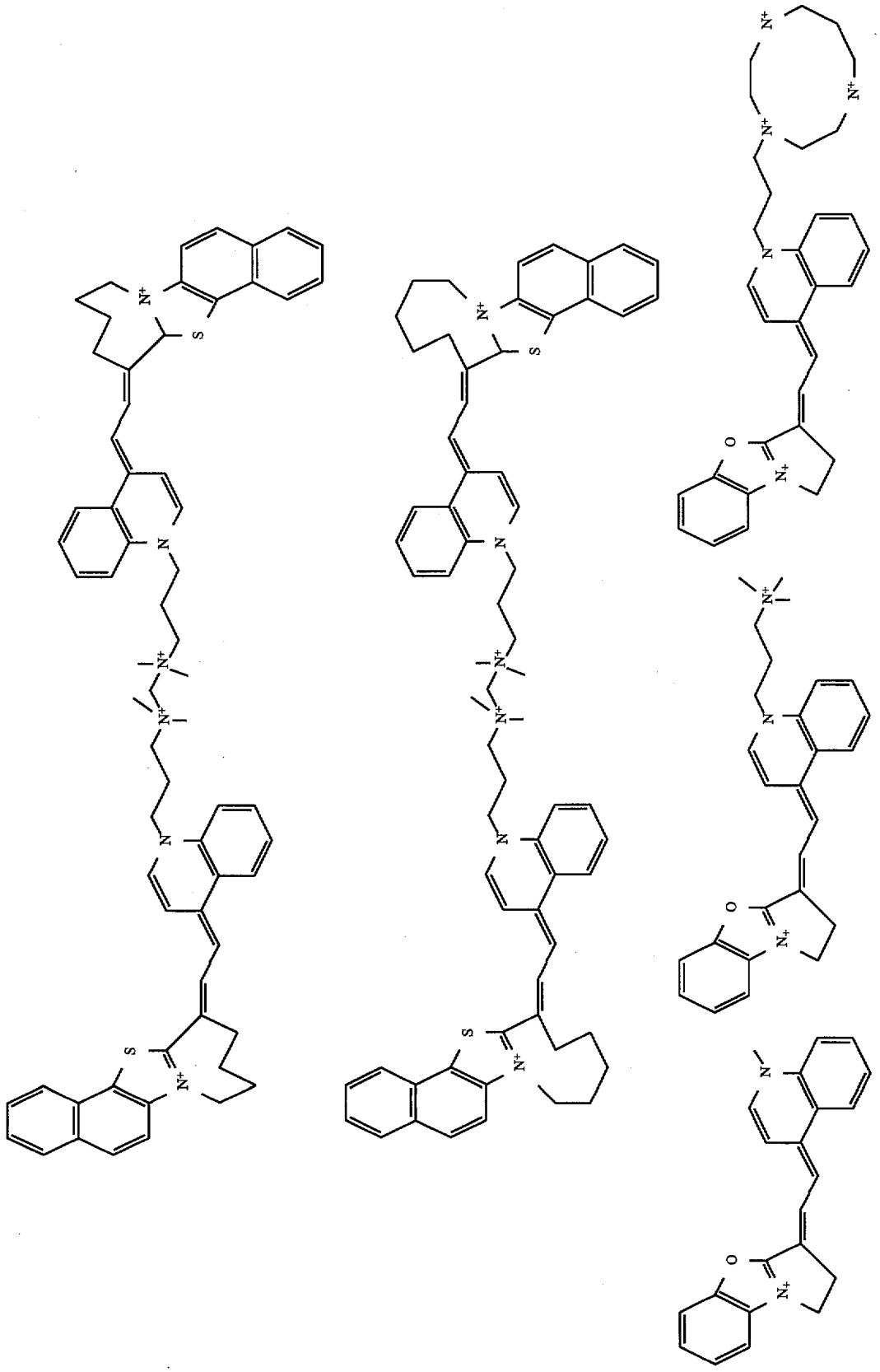

TABLE 2-continued
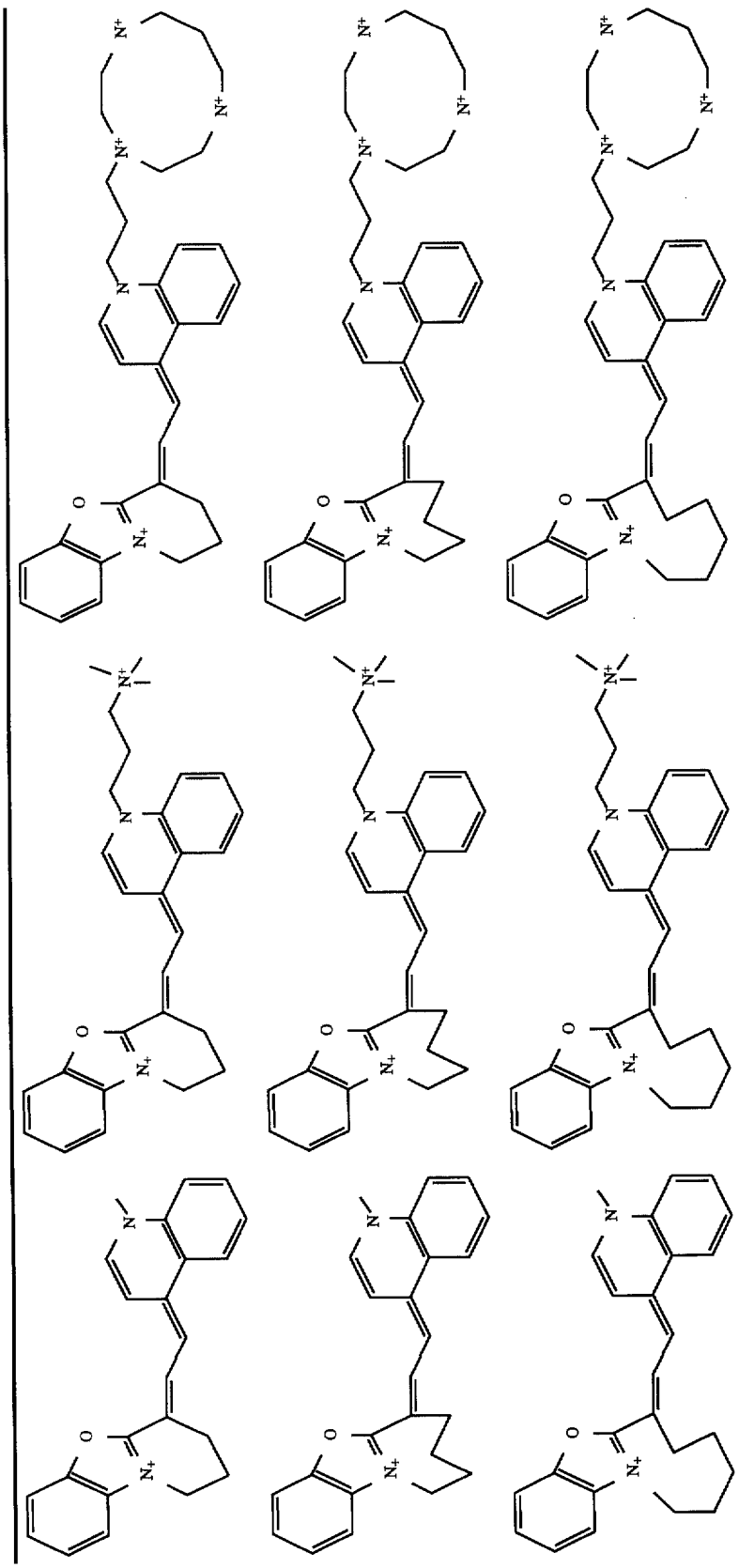

TABLE 2-continued
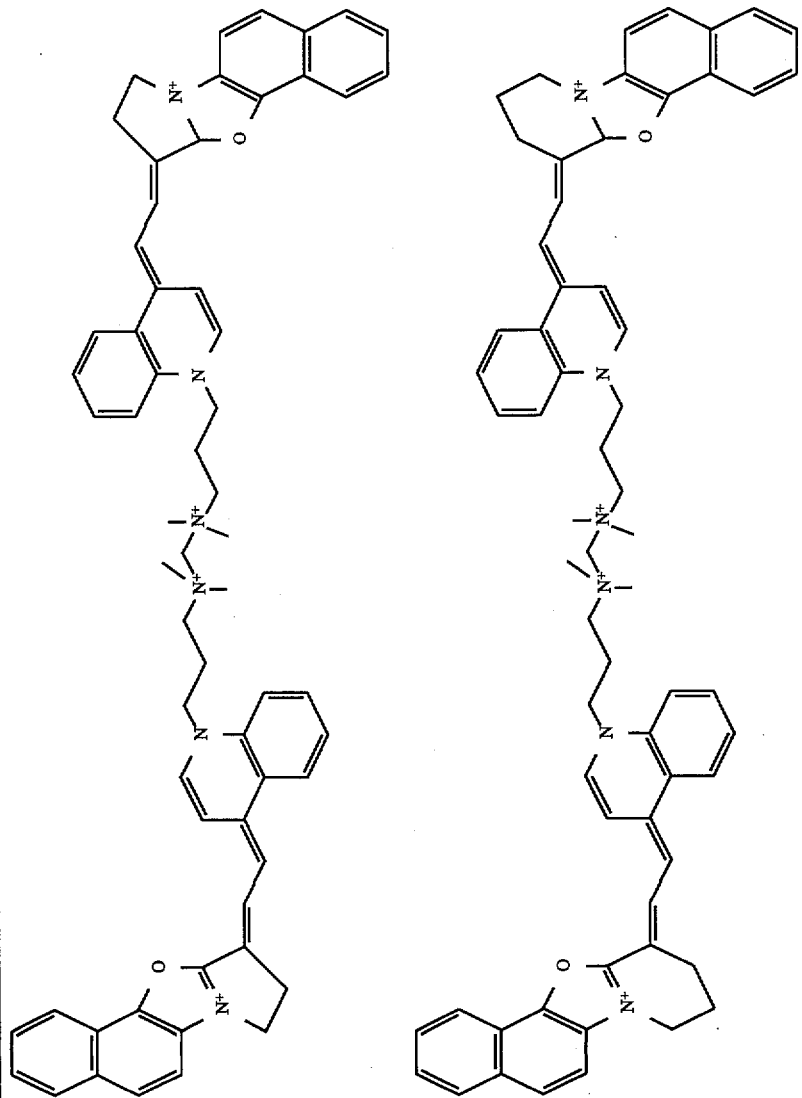

TABLE 2-continued
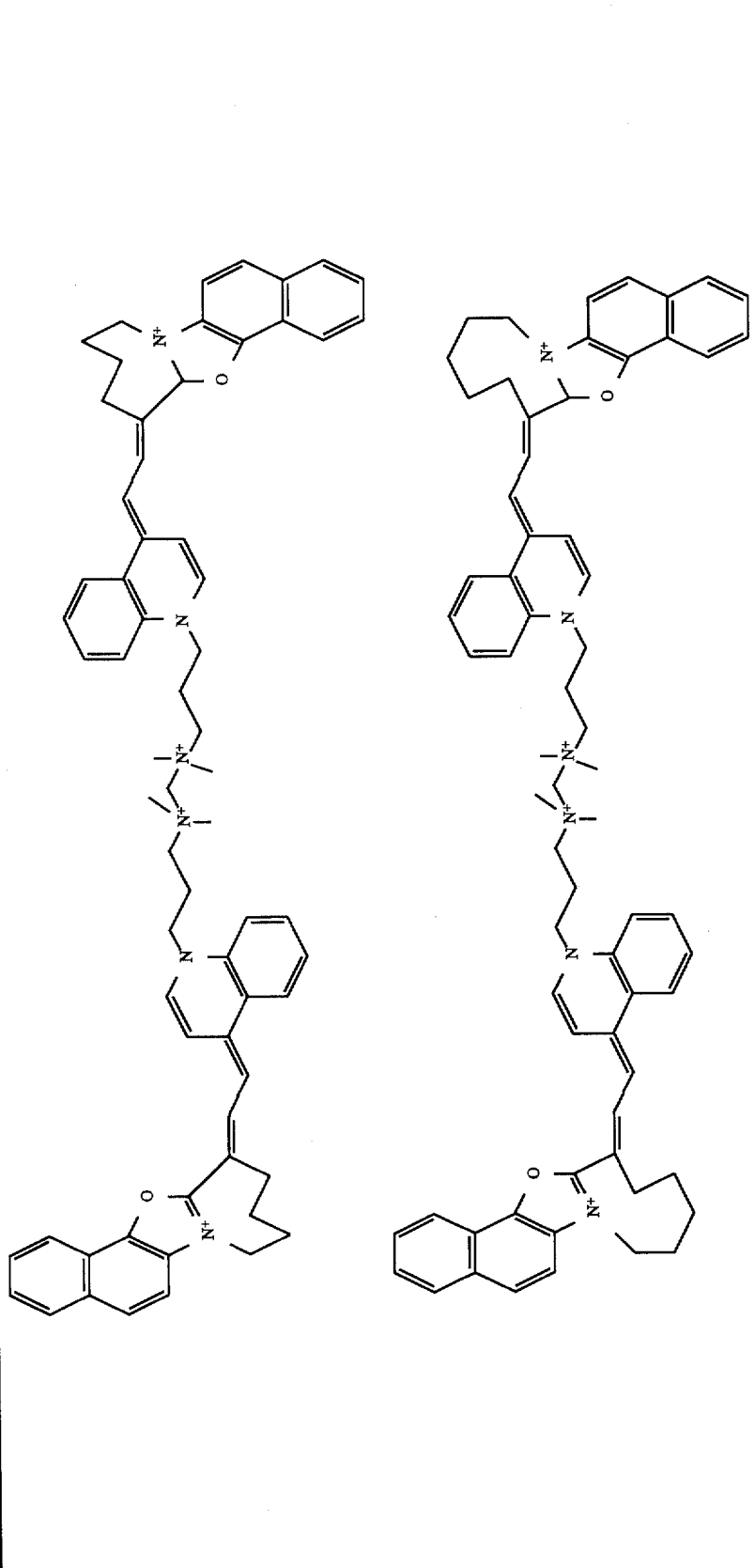

The present invention also relates to fluorescent cyanine dyes having a positively charged substituent attached to the positively charged nitrogen on the benzothiazole portion of the cyanine dye. These fluorescent cyanine dyes are represented by General Formula VI

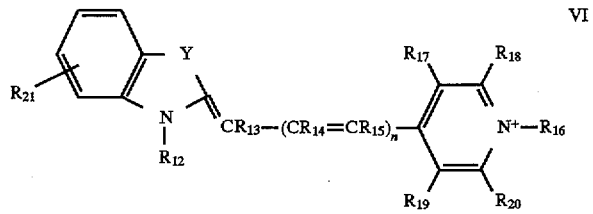

where n is 0, 1 or 2;

Y may be either S or O;

$R_{12}$ is a positively charged alkyl substituent, more preferably a positively charged aminoalkyl substituent;

$R_{13}$, $R_{14}$ and $R_{15}$ may each independently be either hydrogen, $C_1$–$C_{10}$ alkyl, $C_1$–$C_{10}$ alkoxy, or $C_1$–$C_{10}$ alkylthio;

$R_{12}$ and $R_{13}$ may optionally be taken together to form a 5, 6, 7 or 8 membered ring;

$R_{16}$ may be a $C_1$–$C_{50}$ alkyl, preferably substituted with one or more polar substituents which preferably includes one or more positively charged atoms, or a cyclized fluorescent cyanine dye of the present invention, i.e., where $R_{16}$ is a linker between two cyclized fluorescent cyanine dyes;

$R_{17}$ and $R_{18}$ may each independently be either H or $C_{1-10}$ alkyl, or may be taken together to form a 5 or 6 membered ring, most preferably a 5 or 6 membered aromatic ring, optionally substituted with $C_{1-6}$ alkyl or $C_{10}$ alkoxy groups;

$R_{19}$ and $R_{20}$ may each independently be either H or $C_{1-10}$ alkyl, or may be taken together to form a 5 or 6 membered ring, most preferably a 5 or 6 membered aromatic ring, optionally substituted with $C_{1-6}$ alkyl or $C_1$–$C_{10}$ alkoxy groups; and $R_{21}$ may be either H, $C_{1-6}$ alkyl, $C_1$–$C_{10}$ alkoxy or a fused benzene.

As used above, alkyl and alkoxy refer to any substituent having a carbon backbone having the specified range of carbon atoms. The carbon backbone may form a straight chain, may be branched or may be cyclic. The alkyl and alkoxy groups may be optionally substituted by a wide variety of substituents including, for example, alcohols, amines, thiols, phosphates, halides, ethers, esters, ketones, aldehydes, carboxylic acids, amides, cycloalkyls, and aromatic rings.

With regard to n, it is noted that n may equal 1. Accordingly, an embodiment of the present invention includes cyanine dyes having the General Formula VII (i.e. where n=1)

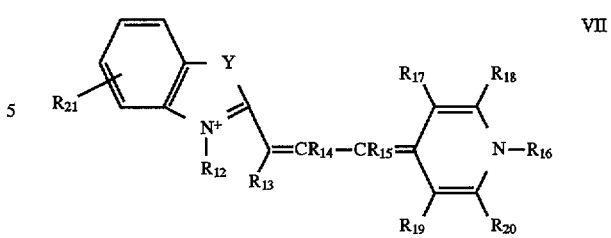

where Y, $R_{12}$, $R_{13}$, $R_{14}$, $R_{15}$, $R_{16}$, $R_{17}$, $R_{18}$, $R_{19}$, $R_{20}$ and $R_{21}$ are as specified above.

With regard to dyes having General Formula VI or VII, Y may be either S or O and is most preferably S.

$R_{12}$ can be an aminoalkyl chain containing a backbone of 3–42 carbons and 1–5 positively charged nitrogen atoms as described in U.S. Pat. No. 5,321,130 to Yue, et al. which is incorporated herein by reference. In addition to the positively charged substituents described in U.S. Pat. No. 5,321,130, $R_{12}$ is also intended to include aminoalkyl chains including a positively charged cyclic aminoalkyl group having 1–5 positively charged nitrogen atoms.

In a preferred embodiment, $R_{12}$ has the general formula —$R_{28}N(R_{29}R_{30}R_{31})$ where $R_{28}$ is a $C_{1-5}$ alkyl and $R_{29}$, $R_{30}$, and $R_{31}$ are each independently a $C_{1-10}$ alkyl.

In an alternate preferred embodiment, $R_{12}$ and $R_{13}$ are taken together to form a 5, 6, 7 or 8 membered ring where the ring includes a positively charged alkyl substituent, more preferably an aminoalkyl chain containing a backbone of 3–42 carbons and 1–5 positively charged nitrogen atoms as described in U.S. Pat. No. 5,321,130 to Yue, et al. Dyes of this embodiment may be generally represented by General Formula VIII

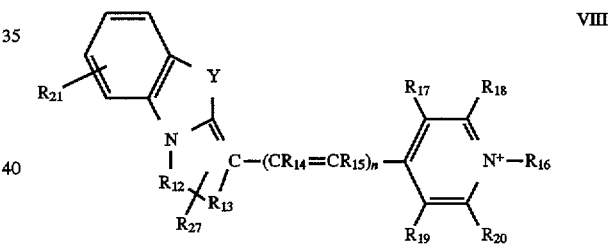

where $R_{12}$ and $R_{13}$ represents the atoms necessary to form a 5, 6, 7 or 8 membered ring and $R_{27}$ is a positively charged substituent, as specified above with regard to $R_{12}$, which may be attached to any atom used to form the 5, 6, 7 or 8 membered ring as represented by $R_{12}$ and $R_{13}$. In this regard, these dyes are equivalent to the dyes described above having the General Formula V.

$R_{14}$ and $R_{15}$ may each independently be either hydrogen, $C_1$–$C_{10}$ alkyl, $C_1$–$C_{10}$ alkoxy, or $C_1$–$C_{10}$ alkylthio, and are preferably H.

$R_{16}$ may be a $C_1$–$C_{50}$ alkyl. Since DNA and RNA to which the cyclized cyanine dyes bind contain negatively charged phosphate backbones, it is preferred that $R_{16}$ be substituted with one or more polar substituents. It is most preferred that $R_{16}$ include one or more positively charged atoms in the polar substituent, such as is specified with regard to $R_{12}$ above.

The cyanine dyes according to General Formula VI, i.e., dyes where a positively charged substituent is positioned off the nitrogen of the benzothiazole portion of the dye, provide the advantage over previous cyanine dyes of exhibiting a significantly larger net fluorescence enhancement with DNA than cyanine dyes where a positively charged substituent is positioned at $R_{16}$ alone.

The use of intercalating dyes for staining cell nuclei requires that the dye itself be membrane-permeable or that a membrane permeabilizing step be incorporated into the sample preparation. In general, dyes with more than one charge are not membrane permeable. Methods for enabling charged molecules and very large molecules into cells include the use of chemicals, such as digitonin, freeze-thaw cell lysis steps, or the use of non-ionic detergents such as TRITON X-100. For speed and simplicity, it is preferred to add approximately 9 mm TRITON X-100.

The presence of a detergent solution (TRITON X-100) causes significant fluorescence enhancement of the dyes as compared to in PBS buffer. An increase in detergent-enhanced fluorescence ($F_{TRITON}/F_{PBS}$) has the effect of decreasing the net DNA enhanced fluorescence over detergent-enhanced background fluorescence ($F_{DNA}/F_{TRITON}$). The detergent-enhanced fluorescence is believed to increase with increasing hydrophobicity.

Fluorescence enhancement of the dyes upon binding to an excess of DNA was found to be fairly constant regardless of how the quinolinium ring side chain was modified ($R_{16}$). Advantageously, however, it was found that inclusion of a positively charged substituent off the positively charged nitrogen of the benzothiazole portion of the dye (General Formula VI) causes the dye to exhibit a significantly larger net DNA-enhancement than the positioning of a positively charged substituent at $R_{16}$ alone. As a result, smaller concentrations of nucleic acids can be detected using cyanine dyes having General Formula VI.

For example, Table 3 compares the fluorescence ratios of dyes in a saline buffer, a detergent (TRITON X-100) and in a DNA solution. Dye solutions (1.0 μM) were prepared in phosphate buffered saline (PBS), in PBS with TRITON X-100 (9 mM), and in PBS with double-stranded DNA (100 μM).

Table 3 shows the effect of various side chains on the fluorescence background in TRITON X-100 (9 mM). As

TABLE 3

Fluorescence Ratios of Dyes in Buffer, TRITON X-100 and DNA Solutions

| Structure | | $F_{TRITON}/F_{PBS}$ | $F_{DNA}/F_{PBS}$ | $F_{DNA}/F_{TRITON}$ |
|---|---|---|---|---|
| 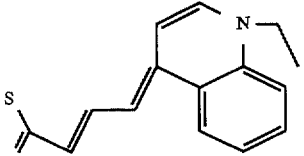 | 6# | 94 | 200 | 3 |
| 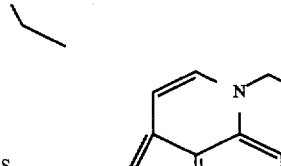 | 5* | 12 | 100 | 8 |
|  | 7* | 10 | 70 | 7 |
| 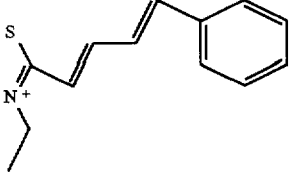 | 8 | 1.8 | 70 | 40 |

*Compounds 5 and 7 are taught in U.S. Pat. No. 5,321,130 to Yue, et al.
Compound 6 is taught in U.S. Pat. No. 4,957,870 to Lee, et al.

illustrated in Table 3, the net DNA enhanced fluorescence over detergent-enhanced background fluorescence ($F_{DNA}/F_{TRITON}$) was found to be a factor of 5 greater in dye 8 than in dye 7. This result is unexpected since the net charge of 3+ is the same for both dyes 7 and 8. It appears that both the location and quantity of charges affect the fluorescence enhancement of the dyes.

The cyanine dyes according to General Formula VI preferably absorb light at a wavelength of at least about 640 nm, more preferably at least about 649 nm and emit fluorescence at a wavelength of at least about 650 nm, more preferably at least about 663 nm. The cyanine dyes also preferably have a positive Stoke's shift ($\lambda_{Emission}-\lambda_{Abs.}$) of at least 11 nm.

Table 4 provides examples of some of the preferred cyanine dyes having General Formula VI. It should be understood, however, that the dyes listed in Table 4 are intended only to exemplify the cyanine dyes of the present invention and are not intended to be limiting.

TABLE 4
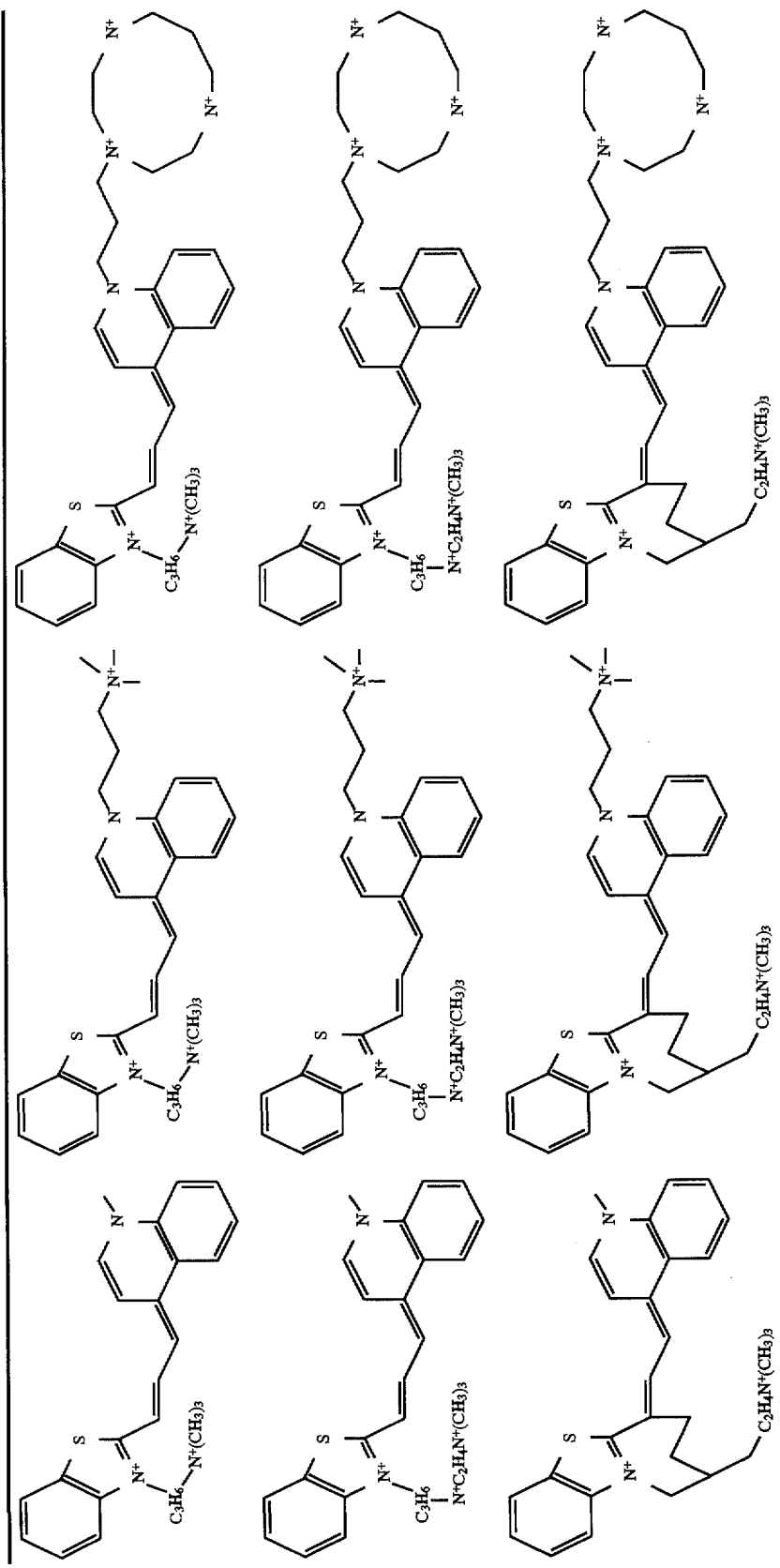

TABLE 4-continued
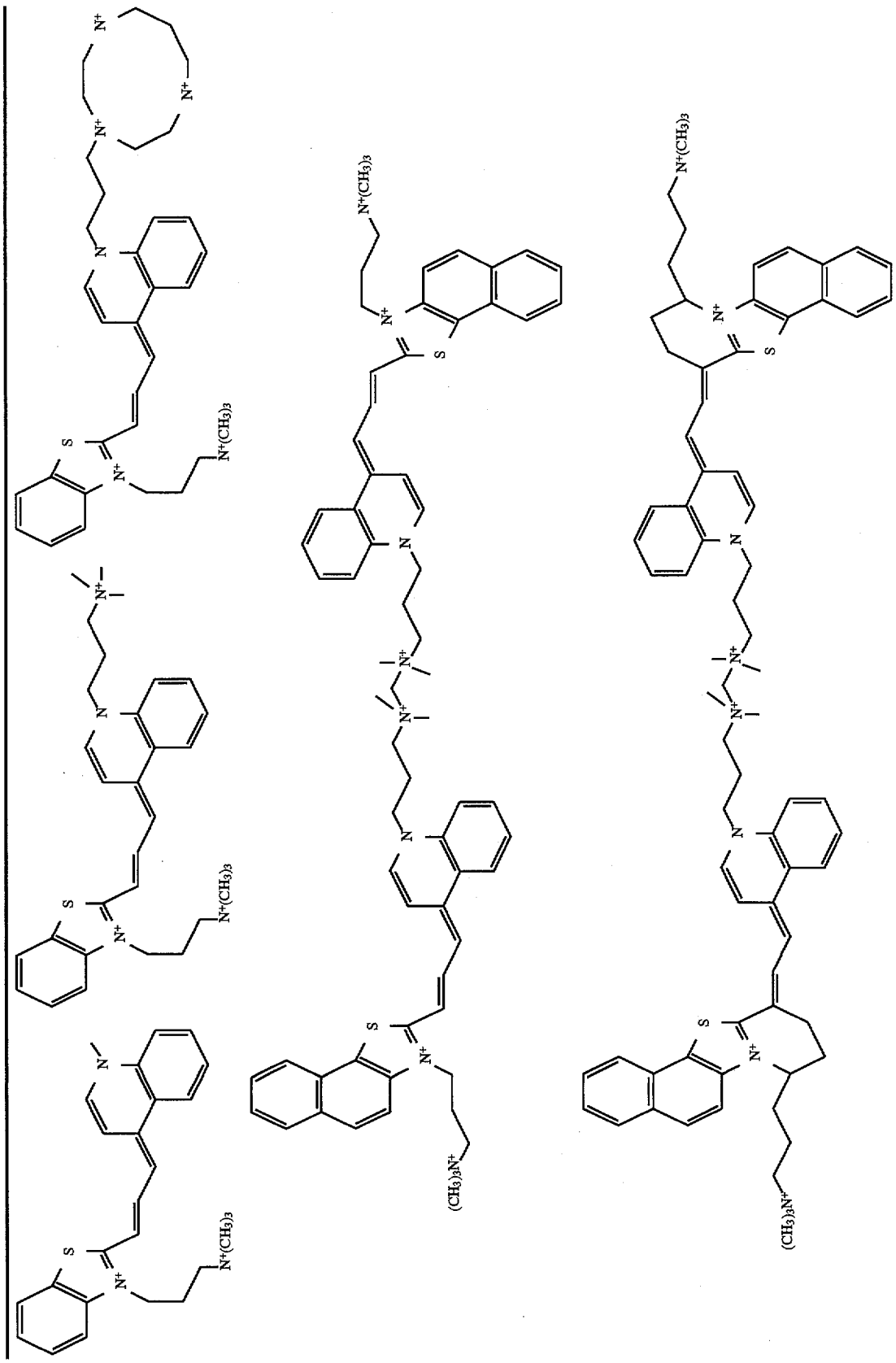

TABLE 4-continued
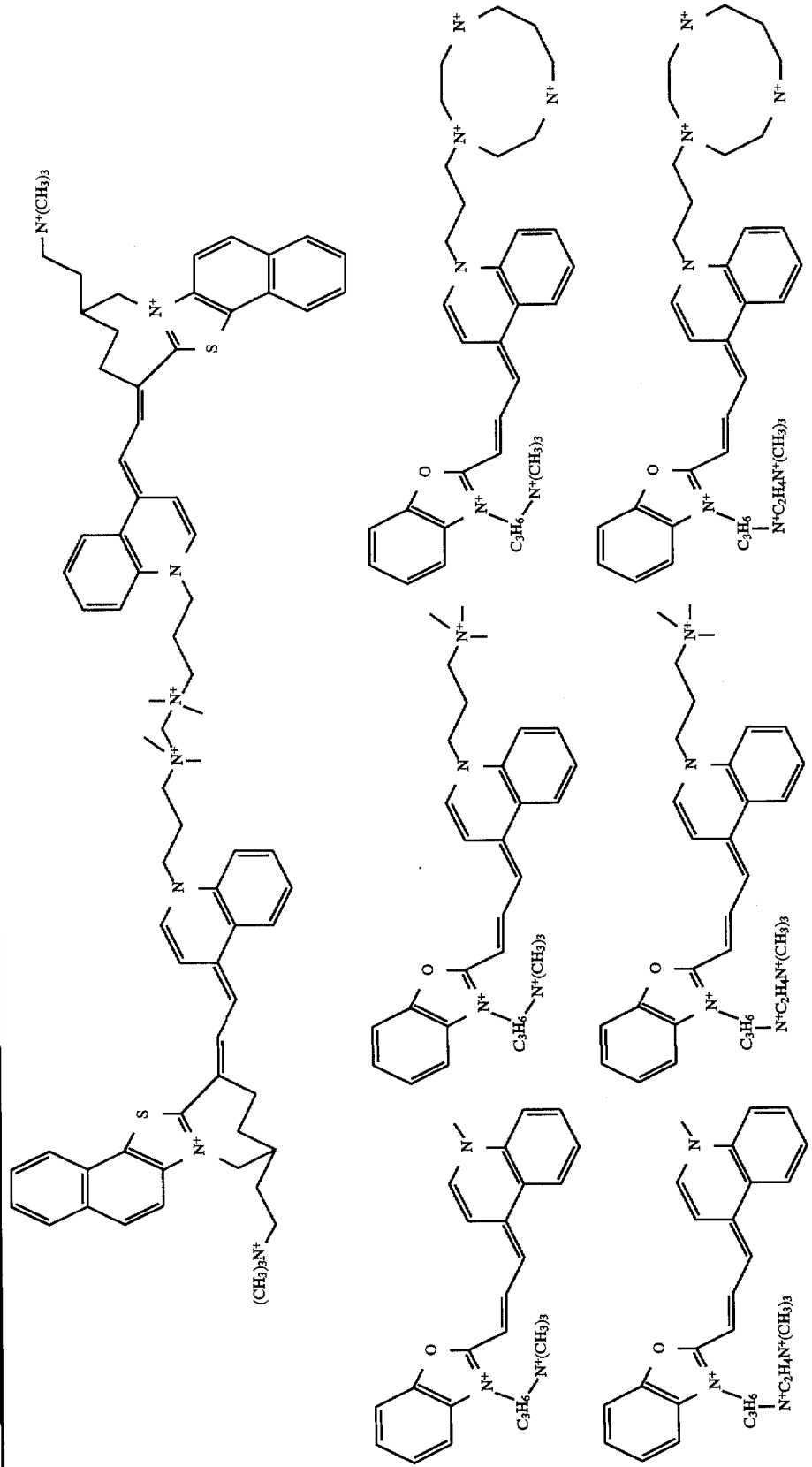

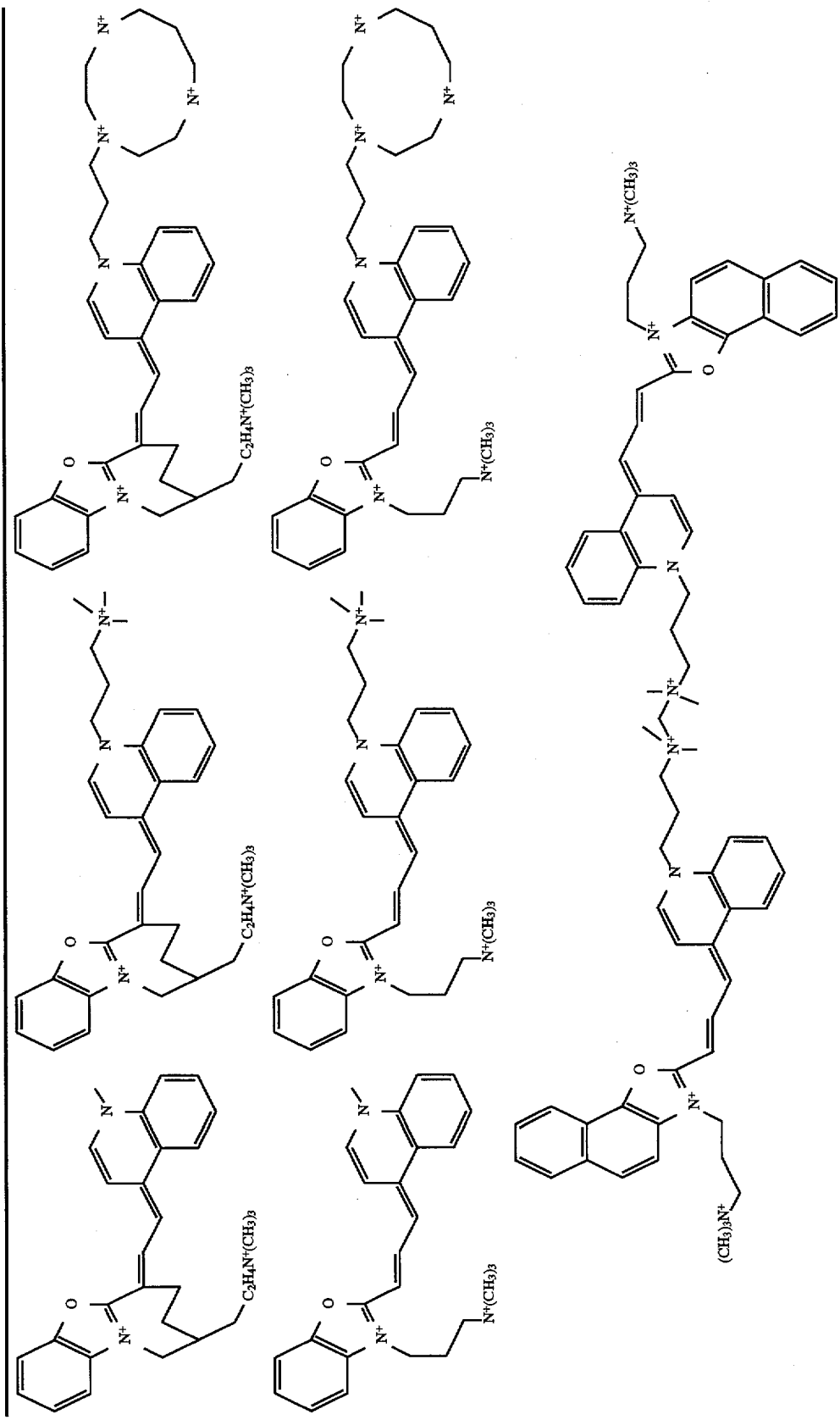

TABLE 4-continued
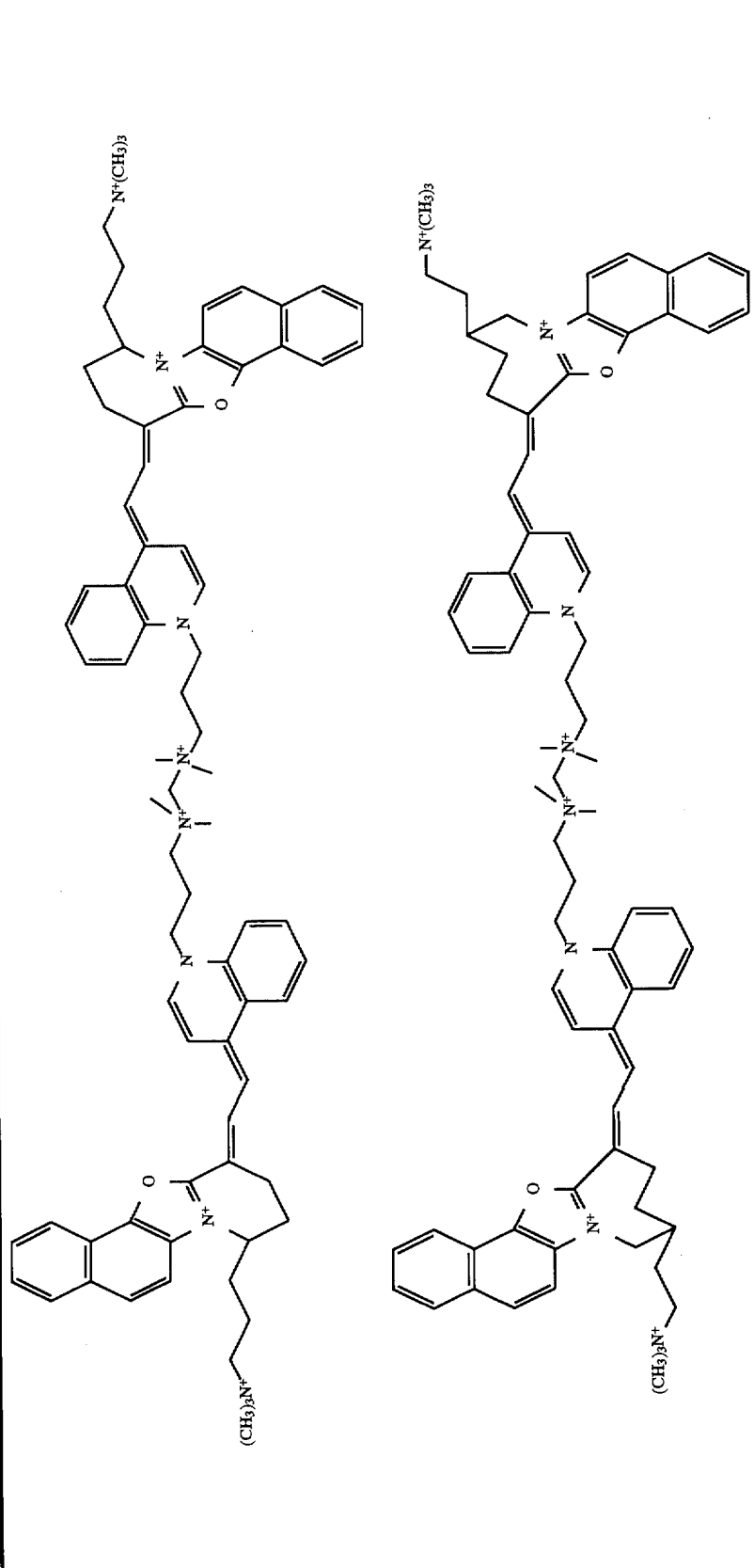

The present invention also relates to the use of the cyanine dyes having General Formulas I, II, IV, V, VI, VII or VIII to form compositions for detecting the presence of nucleic acids in a sample. In general, the compositions include a cyanine dye according to the present invention non-covalently bound to a nucleic acid, i.e., DNA or RNA.

The fluorescence of the cyanine dyes of the present invention significantly increase when bound to a nucleic acid. As a result, it is possible to qualitatively or quantitatively determine the presence of nucleic acids in a sample by monitoring the change in the fluorescence intensity of the dye at a wavelength corresponding to the composition of the dye bound to the nucleic acids. Use of cyanine dyes in general for detecting the presence of nucleic acids in a sample is known in the art. A discussion regarding the use of cyanine dyes to detect the presence of nucleic acids in a sample is provided in U.S. Pat. No. 5,321,130 to Yue, et al. which is incorporated herein by reference.

The present invention also relates to a method for detecting nucleic acids by contacting the nucleic acids with a cyanine dye of the present invention. According to the method, a sample of nucleic acids are contacted with a cyanine dye of the present invention in order to form the composition of a cyanine dye non-covalently bound to a nucleic acid sequence. After the dye-nucleic acid sequence composition is formed, the bound dye is exposed to light having a wavelength near an absorbance maximum of the dye when bound to a nucleic acid sequence. The resulting fluorescence emission of the dye is then detected in order to qualitatively or quantitatively determine the presence of nucleic acids in the sample.

EXAMPLE 1: PREPARATION OF COMPOUND 4

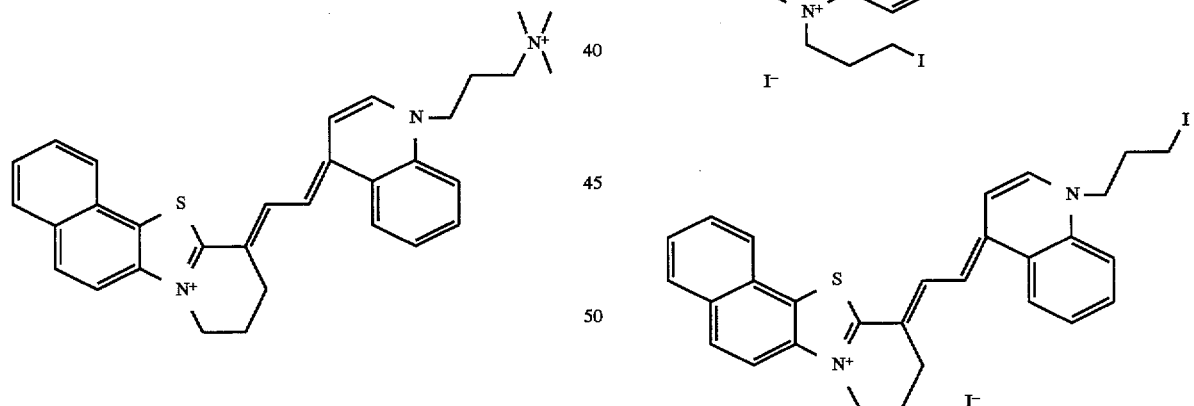

1a. Preparation of 2,3-Tetramethylenenaphth[2,1-d]thiazolium Bromide

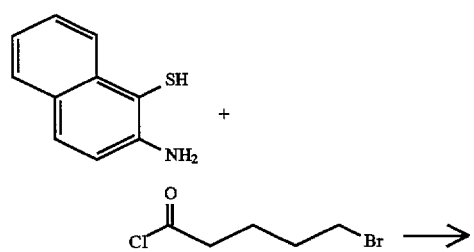

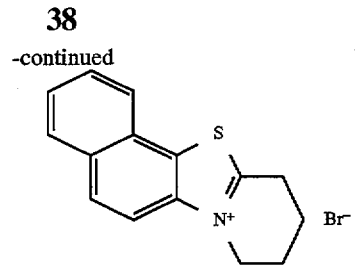

2-Aminonaphthalene-1-thiol was prepared by the method of Ambrogi, et al. (Ambrogi, V.; Grandolini, G.; Perioli, L.; Rossi, C. *Synthesis*, 1992, 7, 656–8.) 2-Aminonaphthalene-1-thiol (0.14 g, 0.8 mmol) and bromovaleryl chloride (0.48 g, 2.4 mmol) were combined and heated to 100° for 1 h, then to 50° C. overnight. The resulting solid was washed with acetone and air-dried to provide a white solid (0.16 g, 0.5 mmol, 60% yield).

1b. Preparation of IodoNAP6

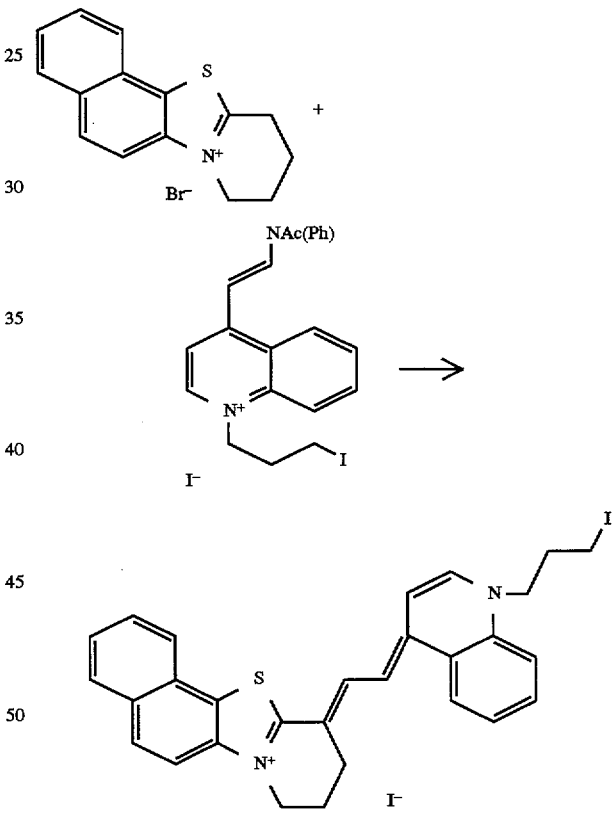

4-(2"-Acetanilidovinyl)-1'-(3'-iodopropyl)-quinolinium iodide (prepared by the general method of Brooker, et al. *J. Am. Chem. Soc.* 1941, 63, 3192–3203; 32 mg, 63 µmol), 2,3-tetramethylenenaphth[2,1-d]thiazolium bromide (20 mg, 63 µmol), triethylamine (40 µL) and ethanol (1 mL) were combined and refluxed for 20 min. The dark blue solid was recrystallized sequentially from isopropanol and ethanol to provide a purple solid (12 mg, 30% yield). HPLC analysis on a C8 reverse-phase column using gradient elution of 40% to 80% acetonitrile vs. 0.1M triethylammonium acetate buffer showed one major peak at 16 min.

1c. Preparation of Compound 4

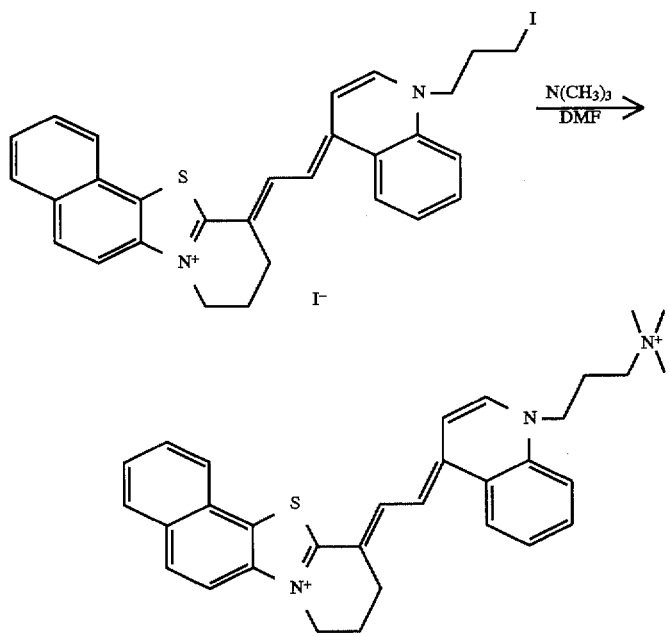

IodoNAP6 (2 mg, 3 μmol) was dissolved in dimethylformamide. Trimethylamine was bubbled through the solution. The reaction was monitored by thin layer chromatography on silica gel with methanol as the eluant. The Rf values of IodoNAP6 and compound 4 were 0.5 and zero, respectively. After 30 min, reaction was complete. The solvent was evaporated and the residue partitioned between methylene chloride ($CH_2Cl_2$) and water. The aqueous layer was washed with 2×1 mL $CH_2Cl_2$ and concentrated to dryness. HPLC analysis with the same gradient that was used with iodoNAP6 showed one broad peak at 7.2 min with no apparent starting material. The absorbance maximum of compound 4 in methanol was at 667 nm.

EXAMPLE 2: PREPARATION OF COMPOUND 8

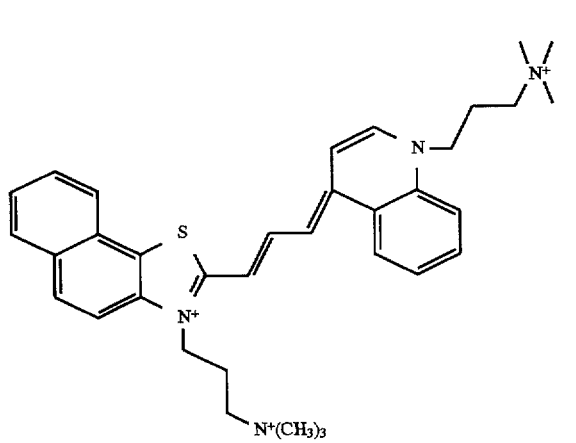

2a. Preparation of 1',1"-(3',3"-Bisiodopropyl)-thia-4-carbocyanine Iodide

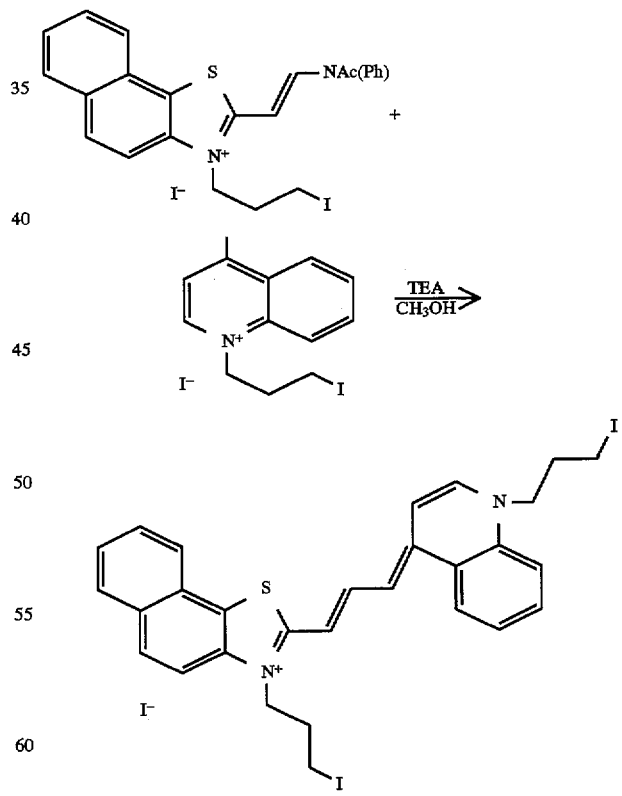

1'-(3'-Iodopropyl)-2-(2"-acetanilidovinyl)-benzothiazium iodide (15 mg, 26 μmol), 1'-(3'-iodopropyl)-quinolinium iodide (15 mg, 34 μmol), triethylamine (50 μL) and methanol (1 mL) were combined at room temperature. A blue precipitate formed immediately. The reaction mixture was centrifuged and the residue washed with methanol and isopropanol and air-dried to provide a dark solid (15 mg, 20 μmol, 77% yield).

2b. Preparation of Compound 8

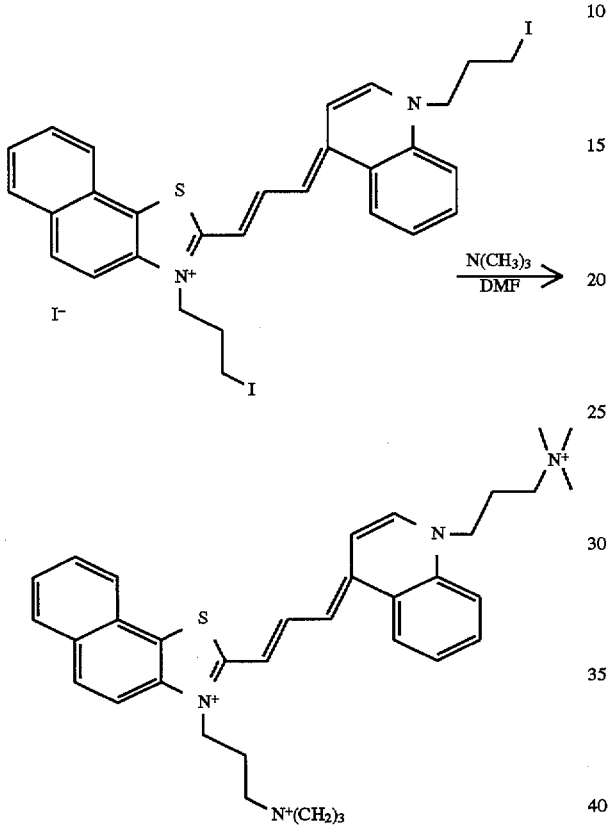

1',1''-(3',3'-Bisiodopropyl)-thia-4-carbocyanine iodide (15 mg, 20 μmol) was dissolved in DMF and trimethylamine bubbled through the solution. The reaction progress was monitored by TLC on reverse-phase plates with 1:1 dimethylformamide:4M NaCl as eluant. The Rf's of the bisiodo starting material and the bisammonium salt were 0 and 0.8, respectively. The intermediate monoammonium salts could also be resolved, at Rf's of 0.7 and 0.6. After 30 min the reaction was complete. The solvent was evaporated. The absorbance maximum of compound 8 in DMSO was at 639 nm.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A fluorescent cyanine dye having the general formula

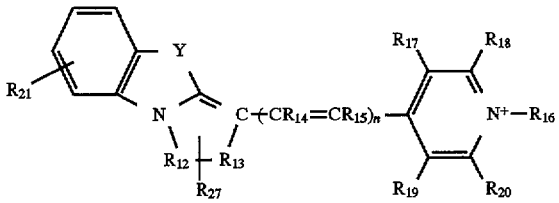

wherein:

n is 0, 1 or 2;

Y is selected from the group consisting of S and O;

$R_{12}$ and $R_{13}$ represent the atoms necessary to form a 5, 6, 7 or 8 membered ring;

$R_{14}$ and $R_{15}$ are each independently selected from the group consisting of hydrogen, $C_1$–$C_{10}$ alkyl, $C_1$–$C_{10}$ alkoxy and $C_1$–$C_{10}$ alkylthio;

$R_{16}$ is a $C_1$–$C_{50}$ alkyl;

$R_{17}$ and $R_{18}$ are each independently selected from the group consisting of H and $C_{1-10}$ alkyl, or are taken together to form a 5 or 6 membered ring;

$R_{19}$ and $R_{20}$ are each independently selected from the group consisting of H and $C_{1-10}$ alkyl, or are taken together to form a 5 or 6 membered ring;

$R_{21}$ is selected from the group consisting of H, $C_{1-6}$ alkyl, $C_1$–$C_{10}$ alkoxy and a fused benzene; and $R_{27}$ is a positively charged alkyl substituent which may be attached to any of the atoms forming the 5, 6, 7 or 8 membered ring as represented by $R_{26}$.

2. The fluorescent cyanine dye of claim 1 wherein $R_{27}$ includes an aminoalkyl chain containing a backbone of 3–42 carbons and 1–5 positively charged nitrogen atoms.

3. The fluorescent cyanine dye of claim 1 wherein $R_{27}$ is a positively charged cyclic aminoalkyl group having 1–5 positively charged nitrogen atoms.

4. The fluorescent cyanine dye of claim 1 wherein $R_{27}$ has the general formula —$R_{28}N(R_{29}R_{30}R_{31})$ where $R_{28}$ is a $C_{1-5}$ alkyl and $R_{29}$, $R_{30}$, and $R_{31}$ are each independently a $C_{1-10}$ alkyl.

5. The fluorescent cyanine dye of claim 1 wherein Y is S.

6. The fluorescent cyanine dye of claim 1 wherein $R_{17}$ and $R_{18}$ or $R_{19}$ and $R_{20}$ are each H.

7. The fluorescent cyanine dye of claim 6 wherein $R_{17}$ and $R_{18}$ or $R_{19}$ and $R_{20}$ are taken together to form a 5 or 6 membered ring.

8. The fluorescent cyanine dye of claim 7 wherein the ring formed by $R_{17}$ and $R_{18}$ or $R_{19}$ and $R_{20}$ is a 6 membered aromatic ring.

9. A composition comprising:

a fluorescent cyanine dye noncovalently bound to a nucleic acid polymer, the fluorescent cyanine dye having the general formula

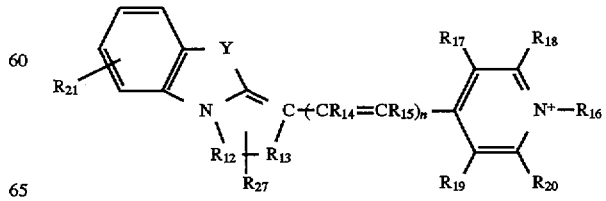

wherein:

43 n is 0, 1 or 2;

Y is selected from the group consisting of S and O;

$R_{12}$ and $R_{13}$ represent the atoms necessary to form a 5, 6, 7 or 8 membered ring;

$R_{14}$ and $R_{15}$ are each independently selected from the group consisting of hydrogen, $C_1-C_{10}$ alkyl, $C_1-C_{10}$ alkoxy and $C_1-C_{10}$ alkylthio;

$R_{16}$ is a $C_1-C_{50}$ alkyl;

$R_{17}$ and $R_{18}$ are each independently selected from the group consisting of H and $C_{1-10}$ alkyl, or are taken together to form a 5 or 6 membered ring;

$R_{19}$ and $R_{20}$ are each independently selected from the group consisting of H and $C_{1-10}$ alkyl, or are taken together to form a 5 or 6 membered ring;

$R_{21}$ is selected from the group consisting of H, $C_{1-6}$ alkyl, $C_1-C_{10}$ alkoxy and a fused benzene; and $R_{27}$ is a positively charged alkyl substituent which may be attached to any of the atoms forming the 5, 6, 7 or 8 membered ring as represented by $R_{12}$ and $R_{13}$.

10. A fluorescent cyanine dye having the general formula

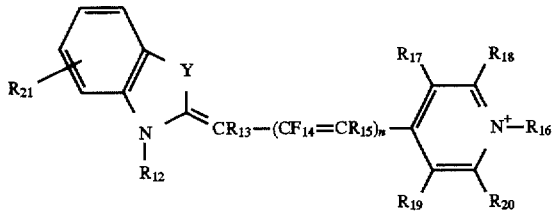

wherein:

n is 0, 1 or 2;

Y is selected from the group consisting of S and O;

$R_{12}$ is a positively charged alkyl substituent;

$R_{13}$, $R_{14}$ and $R_{15}$ are each independently selected from the group consisting of hydrogen, $C_1-C_{10}$ alkyl, $C_1-C_{10}$ alkoxy, and $C_1-C_{10}$ alkylthio;

$R_{16}$ is a $C_1-C_{50}$ alkyl;

$R^{17}$ and $R_{18}$ are each independently selected from the group consisting of H and $C_{1-10}$ alkyl, or are taken together to form a 5 or 6 member ring, $R_{19}$ and $R_{20}$ are each independently selected from the group consisting of H and $C_{1-10}$ alkyl, or are taken together to form a 5 or 6 membered ring;

$R_{17}$ and $R_{18}$ or $R_{19}$ and $R_{20}$ are each H; and $R_{21}$ is selected from the group consisting of H, $C_{1-6}$ alkyl, $C_1-C_{10}$ alkoxy and a fused benzene.

11. A fluorescent cyanine dye having the general formula

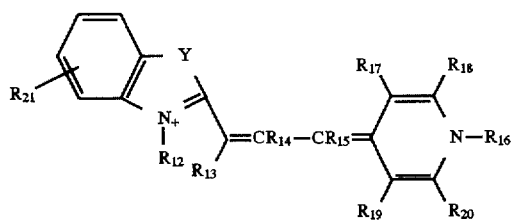

wherein:

Y is selected from the group consisting of S and O;

$R_{12}$ is a positively charged alkyl substituent and includes an aminoalkyl chain containing a backbone of 3–42 carbons and 1–5 positively charged nitrogen atoms;

44

$R_{13}$, $R_{14}$ and $R_{15}$ are each independently selected from the group consisting of hydrogen, $C_1-C_{10}$ alkyl, $C_1-C_{10}$ alkoxy, and $C_1-C_{10}$ alkylthio;

$R_{16}$ is a $C_1-C_{50}$ alkyl;

$R^{17}$ and $R_{18}$ are each independently selected from the group consisting of H and $C_{1-10}$ alkyl, or are taken together to form a 5 or 6 member ring, $R_{19}$ and $R_{20}$ are each independently selected from the group consisting of H and $C_{1-10}$ alkyl, or are taken together to form a 5 or 6 membered ring;

$R_{17}$ and $R_{18}$ are each independently selected from the group consisting of H and $C_{1-10}$ alkyl, or are taken together to form a 5 or 6 membered ring;

$R_{19}$ and $R_{20}$ are each independently selected from the group consisting of H and $C_{1-10}$ alkyl, or are taken together to form a 5 or 6 membered ring; and $R_{21}$ is selected from the group consisting of H, $C_{1-6}$ alkyl, $C_1-C_{10}$ alkoxy and a fused benzene.

12. A fluorescent cyanine dye having the general formula

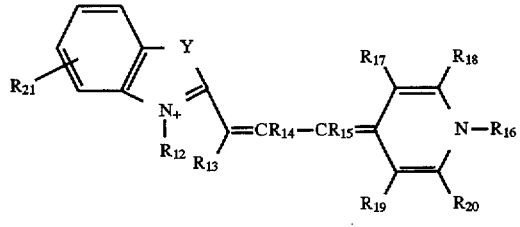

wherein:

Y is selected from the group consisting of S and O;

$R_{12}$ is a positively charged cyclic aminoalkyl group having 1–5 positively charged nitrogen atoms;

$R_{13}$, $R_{14}$ and $R_{15}$ are each independently selected from the group consisting of hydrogen, $C_1-C_{10}$ alkyl, $C_1-C_{10}$ alkoxy, and $C_1-C_{10}$ alkylthio;

$R_{16}$ is a $C_1-C_{50}$ alkyl;

$R_{17}$ and $R_{18}$ are each independently selected from the group consisting of H and $C_{1-10}$ alkyl, or are taken together to form a 5 or 6 membered ring;

$R_{19}$ and $R_{20}$ are each independently selected from the group consisting of H and $C_{1-10}$ alkyl, or are taken together to form a 5 or 6 membered ring; and $R_{21}$ is selected from the group consisting of H, $C_{1-6}$ alkyl, $C_1-C_{10}$ alkoxy and a fused benzene.

13. A fluorescent cyanine dye having the general formula

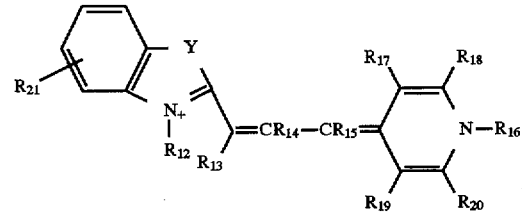

wherein:

Y is selected from the group consisting of S and O;

$R_{12}$ has the general formula —$R_{28}N(R_{29}R_{30}R_{31})$ where $R_{28}$ is a $C_{1-5}$ alkyl and $R_{29}$, $R_{30}$, and $R_{31}$ are each independently a $C_{1-10}$ alkyl;

$R_{13}$, $R_{14}$ and $R_{15}$ are each independently selected from the group consisting of hydrogen, $C_1-C_{10}$ alkyl, $C_1-C_{10}$ alkoxy, and $C_1-C_{10}$ alkylthio;

$R_{16}$ is a $C_1$–$C_{50}$ alkyl;

$R_{17}$ and $R_{18}$ are each independently selected from the group consisting of H and $C_{1\text{-}10}$ alkyl, or are taken together to form a 5 or 6 membered ring;

$R_{19}$ and $R_{20}$ are each independently selected from the group consisting of H and $C_{1\text{-}10}$ alkyl, or are taken together to form a 5 or 6 membered ring; and $R_{21}$ is selected from the group consisting of H, $C_{1\text{-}6}$ alkyl, $C_1$–$C_{10}$ alkoxy and a fused benzene.

14. A fluorescent cyanine dye having the general formula

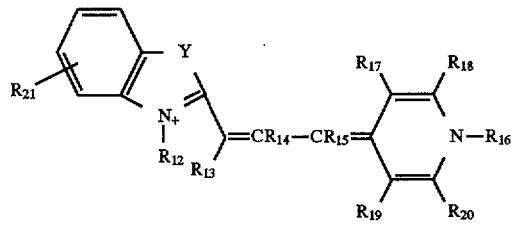

wherein:

Y is selected from the group consisting of S and O;

$R_{12}$ is a positively charged alkyl substituent and includes an aminoalkyl chain containing a backbone of 3–42 carbons and 1–5 positively charged nitrogen atoms;

$R_{13}$, $R_{14}$ and $R_{15}$ are each independently selected from the group consisting of hydrogen, $C_1$–$C_{10}$ alkyl, $C_1$–$C_{10}$ alkoxy, and $C_1$–$C_{10}$ alkylthio;

$R_{16}$ is a $C_1$–$C_{50}$ alkyl;

$R^{17}$ and $R_{18}$ are each independently selected from the group consisting of H and $C_{1\text{-}10}$ alkyl, or are taken together to form a 5 or 6 member ring, $R_{19}$ and $R_{20}$ are each independently selected from the group consisting of H and $C_{1\text{-}10}$ alkyl, or are taken together to form a 5 or 6 membered ring;

$R_{17}$ and $R_{18}$ or $R_{19}$ and $R_{20}$ are each H and are taken together to form a 6 membered aromatic ring;

$R_{19}$ and $R_{20}$ are each independently selected from the group consisting of H and $C_{1\text{-}10}$ alkyl, or are taken together to form a 5 or 6 membered ring; and $R_{21}$ is selected from the group consisting of H, $C_{1\text{-}6}$ alkyl, $C_1$–$C_{10}$ alkoxy and a fused benzene.

* * * * *

UNITED STATES PATENT AND TRADEMARK OFFICE
CERTIFICATE OF CORRECTION

PATENT NO. : 5,734,058
DATED : Mar. 31, 1998
INVENTOR(S) : Linda G. Lee

It is certified that error appears in the above-identified patent and that said Letters Patent is hereby corrected as shown below:

Title page, References Cited, U.S. PATENT DOCUMENTS, 5,436,134 7/1995, change "Haughland", to read --Haugland--.

Column 43, line 27 or 28, change "$CF_{14}$", to read --$ERCR_{14}$--.

Signed and Sealed this

Thirtieth Day of June, 1998

Attest:

BRUCE LEHMAN

Attesting Officer

Commissioner of Patents and Trademarks